United States Patent [19]

Moberg

[11] Patent Number: 5,016,630

[45] Date of Patent: May 21, 1991

[54] HEART PACEMAKER WITH HYSTERESIS FUNCTION

[75] Inventor: Lennart Moberg, Spanga, Sweden

[73] Assignee: Siemens Aktiengesellschaft, Munich, Fed. Rep. of Germany

[21] Appl. No.: 302,978

[22] Filed: Jan. 30, 1989

[30] Foreign Application Priority Data

Feb. 1, 1988 [EP] European Pat. Off. ............ 88101405

[51] Int. Cl.[5] .............................................. A61N 1/362
[52] U.S. Cl. ............................................... 128/419 PG
[58] Field of Search .................................. 128/419 PG

[56] References Cited

U.S. PATENT DOCUMENTS

| | | | |
|---|---|---|---|
| 3,857,399 | 12/1974 | Zacouto | 128/419 PG |
| 4,052,991 | 10/1977 | Zacouto | 128/419 PG |
| 4,163,451 | 8/1979 | Lesnick et al. | 128/419 PG |
| 4,169,480 | 10/1979 | Digby et al. | 128/419 PG |
| 4,192,316 | 3/1980 | Walters et al. | 128/419 PG |
| 4,228,803 | 10/1980 | Rickards | 128/419 PG |
| 4,318,411 | 3/1982 | Elmovist | 128/419 PG |
| 4,467,807 | 8/1984 | Bornzin | 128/419 PG |
| 4,503,857 | 3/1985 | Boute et al. | 128/419 PG |
| 4,776,338 | 10/1988 | Lekholm et al. | 128/419 PG |
| 4,856,523 | 8/1989 | Sholder et al. | 128/419 PG |

*Primary Examiner*—William E. Kamm
*Assistant Examiner*—Kennedy J. Schaetzle
*Attorney, Agent, or Firm*—Hill, Van Santen, Steadman & Simpson

[57] ABSTRACT

A heart pacemaker normally operates at a basic pacing rate having a basic escape interval between pacing pulses associated therewith, so that the pulses are delivered at the basic rate in the absence of a sensed, pacer inhibiting heart event. The pacemaker includes circuitry for setting a hysteresis interval, added to the basic escape interval, to form an extended escape interval in response to the sensed, pacer inhibiting heart event, with the hysteresis interval being a function of the basic escape interval length.

3 Claims, 1 Drawing Sheet

HEART PACEMAKER WITH HYSTERESIS FUNCTION

BACKGROUND OF THE INVENTION

1. Field of the Invention

This invention relates to a cardiac pacer or a defibrillator with a pacing function for pacing the human heart. More particularly the invention relates to a pacer including a hysteresis function in accordance with the preamble of claim 1.

2. Description of the Prior Art

Many pacer patients exhibit periods of normal heart sinus rhythm, where natural atrial - ventricular synchrony, sequential AV pumping and good hemodynamics are maintained.

Should the natural heart rate drop for some reason, the depolarization of the ventricle is taken over by the pacer (single chamber or dual chamber in, e.g., VVI-mode). In this situation the AV-synchrony is no longer maintained and the atrial contribution (15-20%) to the cardiac output is lost, thus the pumping capacity of the heart is reduced.

By creating a difference between the programmed pacer basic escape interval, i.e., the interval following paced heartbeats, and the escape interval following a pacer inhibiting, sensed spontaneous (natural) heartbeat, in the sense that the patients with periods of normal sinus rhythm will remain in their own rhythm and thus benefit from the advantages of AV-synchrony.

This difference between sensed and paced intervals is known as hysteresis. For reasons other than that just described, hysteresis can be important. As the pacer is inhibited for longer periods of time, pacer longevity is increased. Further, when sinus rhythm is favored, competition between natural and paced rhythm is reduced.

In modes other than VVI and VVT, the hysteresis function can be employed for favoring the patient's own rhythm. A patient with an atrial synchronized pacer as well as a dual chamber pacer operating in the AAI, AAT or DDD mode can benefit from the above advantages. In these modes, the hysteresis function is applied to the atrial escape interval.

The conventional hysteresis function extends the escape interval following a sensed heart signal by introducing, as in Siemens-Elema's Pulse Generator 704, a fixed hysteresis interval. This interval could be programmable, and technically realized by programming a second (higher) trigger level into the escape interval counter. A more detailed explanation is found in Siemens brochure A91003-M3372-L772-02-7600, published March 1985.

With the advent of rate responsive (RR) pacers, the fixed interval hysteresis could generate rather strange effects. In an RR-pacer the sensor signal sets the basic stimulation rate (basic escape interval) within a wide rate range, typically 30-150 beats/min (bpm), depending on the workload. At 60 bpm, a 250 ms hysteresis time extends the escape interval so that the corresponding rate is 48 bpm. At 150 bpm, when the rate is increased due to increased workload, the same hysteresis time extends the escape interval so that the corresponding rate is 92 bpm.

This large difference at 150 bpm between the interval after pacing and the interval after sensing is inconvenient for the patient as it corresponds to a large drop in heart rate, which does not take the high work load into account. Consequently, the blood pressure goes down and the patient feels dizzy and may faint.

SUMMARY OF THE INVENTION

It is an object of the present invention to provide a rate responsive pacer with an improved hysteresis function which avoids the prior art problem with a fixed hysteresis interval.

It is further object of the present invention to provide an alternative to the fixed hysteresis interval setting in conventional pacers, i.e. pacers which are not of the rate responsive type.

To resolve the prior art problem the present invention consists of a pacemaker having a hysteresis interval which is a function of the basic escape interval. In this way, the hysteresis is related to the actual pacing rate. Preferably, as a percentage hysteresis, the hysteresis interval is the same for the whole range of rates in terms of percentage of the actual basic escape interval. For example, referring to the example given above, 250 ms at 60 bpm (1000 ms) is an extension of 25%. At 150 bpm (400 ms) the same percentage extension (25% × 400 ms = 100 ms), would result in an extended escape interval of 500 ms corresponding to a rate of 120 bpm.

Functional relationships other than percentage could be employed, for example, the inverted escape interval expressed as beats per minute could be used. The embodiment illustrating the invention in the discussion below, refers however to percentage.

Although primarily directed to the resolution of the prior art problem with a fixed hysteresis interval for a rate responsive pacer, it is clear that the present invention also applies to non-rate responsive pacers, where setting of the hysteresis interval as a function of the basic escape interval could be employed as an option or an alternative to fixed interval setting. Only basic escape interval setting is then required as the hysteresis interval follows therefrom, and the invention therefore provides a simplification of the initial hysteresis interval setting. The initial setting could, of course, if necessary, be replaced by a setting selected by the physician with regard to the individual patient's needs.

The foregoing and other objects, features and advantages of the invention will be apparent from the following more particular description of the preferred embodiment of the invention, as illustrated in the accompanying drawings.

DESCRIPTION OF THE PREFERRED EMBODIMENTS

Figure 1:
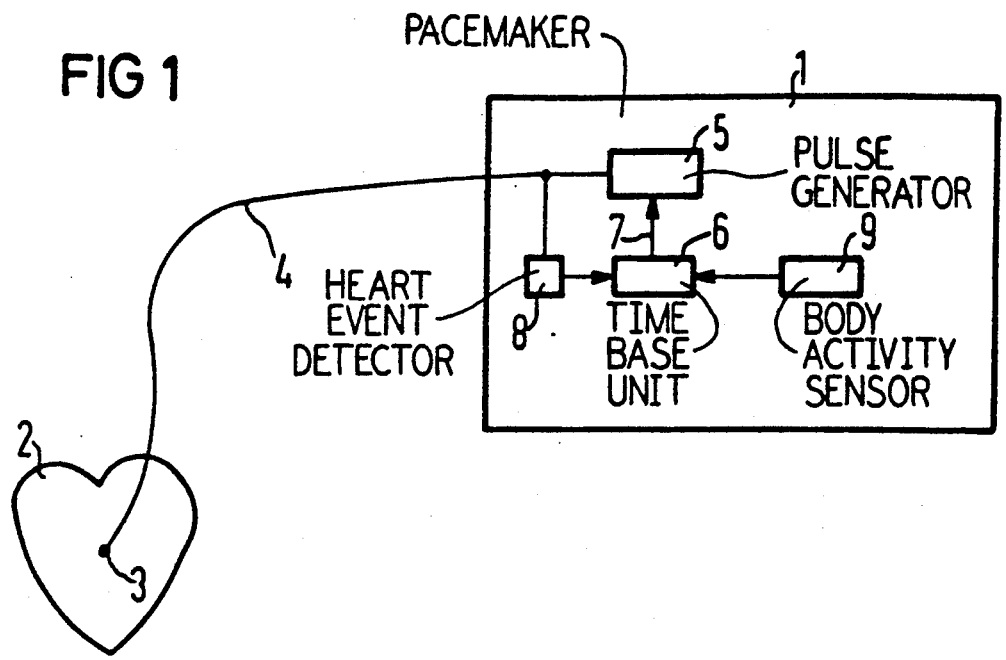
FIG. 1 shows the invention in a schematic block diagram.

In FIG. 1 a human heart is generally designated at 2, and this heart has to be paced by a pacer 1. A pacing/sensing electrode 3 is inserted in the human heart 2 in a manner and position so that the heart can be most efficiently paced. The pacing/sensing electrode 3 is connected through a pacing/sensing lead 4 with a pacing pulse generator 5. A time base unit 6 controls the pacing rate of the pacing pulse generator 5 through line 7. Heart events are sensed by a detector 8 and a body activity related variable, such as activity, temperature, blood oxygen saturation, pH-value and Qt-interval, is sensed by a sensor 9. It should be understood that pacer 1 is capable of pacing/sensing in either/both the atrium or/and the ventricle.

Figure 2:
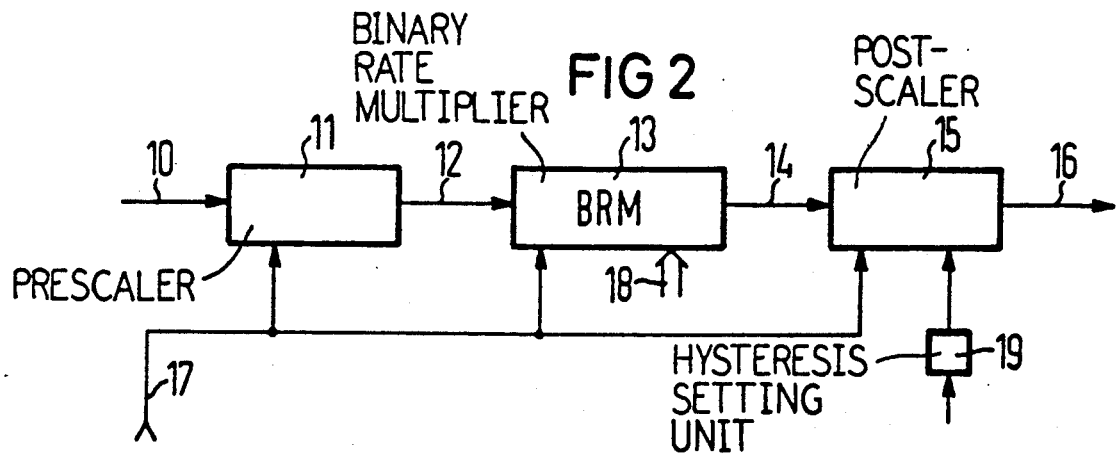
FIG. 2 shows a block diagram of the time base unit in a pacer according to the invention.

The time base unit 6 (FIG. 2) creates the different basic escape intervals using a BRM (Binary Rate Multiplier) 13. For example, the BRM 13 may be an 8-bit BRM having a highest clock rate of 512 Hz (1.953 ms) and a lowest clock rate of 2 Hz (500 ms). The different basic escape intervals are then calculated with these rates as a basis. The time base unit 6 has a pacer clock (not shown) which delivers pulses at 4096 Hz on line 10. A prescaler 11 reduces the pacer clock frequency to 512 Hz, which is the frequency supplied to the BRM 13 on line 12. The BRM 13 produces pulses at a rate depending on the value of a control data word (CDW) on line 18. The pulses produced by the BRM 13 are supplied on line 14 to a post-scaler 15, which counts the pulses. When the count equals 96, a stimulation pulse is produced on line 16, according to formulae (1) and (2).

$$\text{Escape interval time} = 256/X \times 1.953 \text{ ms} \times 96 \quad (1)$$

where $X = $ BRM control data word $0 < X < 256$.

$$\text{Stimulation pulse rate} = 60 \times X/48 \text{ impulses/min.} \quad (2)$$

The basic rate (imp/min) and basic escape interval (time) in milliseconds for different CDW values X are given in table 1.

TABLE 1

| X | Time (ms) | imp/min |
|---|---|---|
| 24 | 2000 | 30 |
| 28 | 1714 | 35 |
| 32 | 1500 | 40 |
| 36 | 1333 | 45 |
| 40 | 1200 | 50 |
| 44 | 1091 | 55 |
| 48 | 1000 | 60 |
| 52 | 923 | 65 |
| 56 | 857 | 70 |
| 60 | 800 | 75 |
| 64 | 750 | 80 |
| 68 | 706 | 85 |
| 72 | 667 | 90 |
| 76 | 632 | 95 |
| 80 | 600 | 100 |
| 84 | 571 | 105 |
| 88 | 545 | 110 |
| 92 | 522 | 115 |
| 96 | 500 | 120 |
| 100 | 480 | 125 |
| 104 | 462 | 130 |
| 108 | 444 | 135 |
| 112 | 429 | 140 |
| 116 | 414 | 145 |
| 120 | 400 | 150 |
| 124 | 387 | 155 |
| 128 | 375 | 160 |
| 132 | 364 | 165 |
| 136 | 353 | 170 |
| 140 | 343 | 175 |
| 144 | 333 | 180 |
| 148 | 324 | 185 |

Different hysteresis intervals can now be added to these (basic) escape intervals by increasing the limit count of the post-scaler 15. The escape interval can be extended, e.g., 10% by counting 10% more pulses, viz. 106 pulses instead of 96. The hysteresis function is activated each time a natural heart event is sensed outside the pulse generator refractory time, i.e. the reset line 17 becomes active and the post-scaler 15 takes the percentage set in hysteresis unit 19 into account.

Different programmable hysteresis intervals are illustrated in table 2 and resulting rates are listed in table 3.

TABLE 2

| Hysteresis (% of basic escape interval time) | Number of pulses counted by the post-scaler |
|---|---|
| 0 | 96 |
| 10 | 106 |
| 15 | 110 |
| 25 | 120 |

TABLE 3

| Rate (imp.min) | Time (ms) | Hysteresis (%) | Time (ms) | Rate (hysteresis) |
|---|---|---|---|---|
| 30 | 2000 | 10 | 2000 | 27 |
|  |  | 15 | 2300 | 26 |
|  |  | 25 | 2500 | 24 |
| 70 | 850 | 10 | 942 | 64 |
|  |  | 15 | 986 | 61 |
|  |  | 25 | 1071 | 56 |
| 100 | 600 | 10 | 660 | 91 |
|  |  | 15 | 690 | 87 |
|  |  | 25 | 750 | 80 |
| 150 | 400 | 10 | 440 | 136 |
|  |  | 15 | 460 | 130 |
|  |  | 25 | 500 | 120 |

Figure 3:
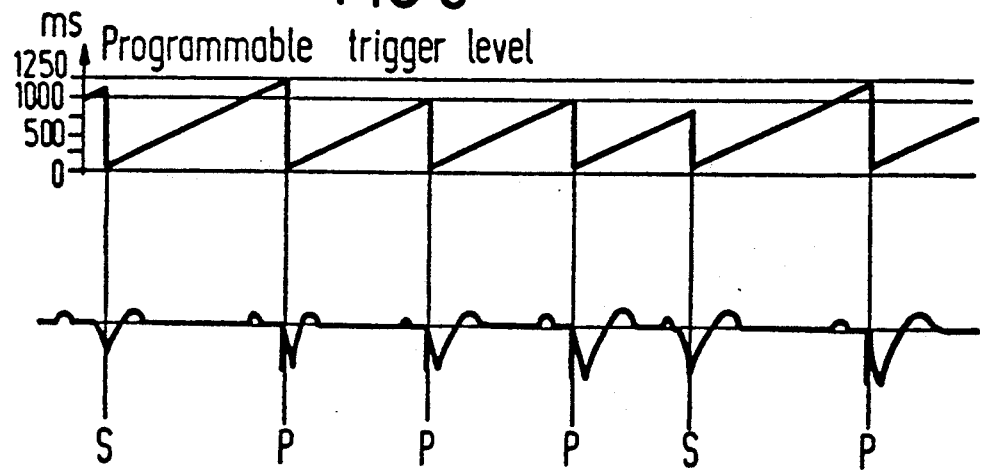
FIG. 3 illustrates the operation of the escape interval counter for sensed and paced hear events.

The hysteresis effect is illustrated in FIG. 3. The figure shows, for different heart events, viz. sensed natural heart events S and paced heart events P, the operation of the escape interval counter programmable at two different triggering levels, and the resulting ECG diagram (middle part of the figure) including the pacing pulses.

The basis rate is 60 imp/min and the percentage hysteresis 25%, viz. the escape interval counter is triggered at two levels, the first one being 1000 ms occurring after a paced heart event P, and the second one being 125% × 1000 ms = 1250 ms occurring after a sensed natural heart event S.

Although modifications and changes may be suggested by those skilled in the art it is the intention of the inventors to embody within the patent warranted hereon all changes and modifications as reasonably and properly come within the scope of their contribution to the art.

I claim as my invention:

1. A pacemaker for stimulating a human heart in a patient comprising:
   means for generating stimulating pulses;
   means for supplying said stimulating pulses to the heart;
   means for sensing a heart event and inhibiting pulse generation upon the sensing of said heart event;
   time base means for controlling said means for generating pulses to produce a basic escape interval between pulses so that said pulses are supplied to said heart at a basic rate in the absence of said heart event; and
   means in said time base means for adding a hysteresis interval, calculated as a fixed percentage of said basic escape interval, to said basic escape interval to form an extended escape interval upon the sensing of said heart event.

2. A pacemaker as claimed in claim 1 further comprising:
   means for sensing a body activity related parameter; and means for varying said basic escape interval as a function of the sensed body activity related parameter.

3. A pacemaker for stimulating a human heart in a patient comprising:

means for generating stimulating pulses;

means for supplying said stimulating pulses to the heart;

means for sensing a heart event and inhibiting pulse generation upon the sensing of said heart event;

time base means for controlling said means for generating pulses to produce a basic escape interval between pulses so that said pulses are supplied to said heart at a basic rate in the absence of said heart event, said time base means including binary into multiplier means for generating pulses at a selected rate in response to a control data word supplied thereto, and means for counting the pulses generated by said binary rate multiplier means; and p1 means in said time base means for adding a hysteresis interval, determined as a function of said basic escape interval, to said basic escape interval to form an extended escape interval upon the sensing of said heart event, said means for setting and adding a hysteresis interval including means for calculating said hysteresis interval as a percentage of the pulse count of said binary rate multiplier means.

* * * * *